(12) United States Patent
Zhang

(10) Patent No.: US 12,102,775 B2
(45) Date of Patent: Oct. 1, 2024

(54) URETERAL CATHETER STRUCTURE

(71) Applicant: Scivita Medical Technology Co., Ltd., Jiangsu (CN)

(72) Inventor: Yi Zhang, Jiangsu (CN)

(73) Assignee: Scivita Medical Technology Co., Ltd., Suzhou (CN)

(*) Notice: Subject to any disclaimer, the term of this patent is extended or adjusted under 35 U.S.C. 154(b) by 819 days.

(21) Appl. No.: 17/291,771

(22) PCT Filed: Jun. 13, 2019

(86) PCT No.: PCT/CN2019/091126
§ 371 (c)(1),
(2) Date: May 6, 2021

(87) PCT Pub. No.: WO2020/093698
PCT Pub. Date: May 14, 2020

(65) Prior Publication Data
US 2021/0386967 A1  Dec. 16, 2021

(30) Foreign Application Priority Data
Nov. 9, 2018 (CN) .......................... 201811329058.5

(51) Int. Cl.
*A61M 25/00* (2006.01)
*A61L 29/02* (2006.01)
(Continued)

(52) U.S. Cl.
CPC .......... *A61M 25/0053* (2013.01); *A61L 29/02* (2013.01); *A61L 29/041* (2013.01);
(Continued)

(58) Field of Classification Search
CPC .......... A61M 25/0053; A61M 25/0045; A61M 2025/0059; A61M 25/005
See application file for complete search history.

(56) References Cited

U.S. PATENT DOCUMENTS

2005/0197536 A1  9/2005  Banik et al.

FOREIGN PATENT DOCUMENTS

| CN | 1723835 A | 1/2006 |
| CN | 103706017 A | 4/2014 |

(Continued)

*Primary Examiner* — Leslie R Deak

(57) ABSTRACT

A ureteral catheter structure, comprising a catheter body (1). The catheter body (1) comprises a stepped braided tube (2), a bending tube (3), and a plastic catheter tip (14) which are spliced with each other. A first stainless steel outer tube (4) supports and connects the stepped braided tube (2) and the bending tube (3) at a splice therebetween, and a first PET heat-shrinkable film (5) is coated on the first stainless steel outer tube (4). A second stainless steel outer tube (6) supports and connects the bending tube (3) and the plastic catheter tip (14) at a position therebetween, and a second PET heat-shrinkable film (7) is coated on the second stainless steel outer tube (6). A traction wire (8) is provided within the catheter body (1), an end of the traction wire (8) being fixed on the bending tube (3), while the other end passing through the stepped braided tube (2). A heat-shrinkable sleeve (9) is provided outside the bending tube (3). An end of the ureteral catheter may be independently bent in multiple sections, thereby achieving a good detection effect, and solving the technical problem of instability when an end of the ureteral catheter is deflected.

10 Claims, 10 Drawing Sheets

(51) Int. Cl.
*A61L 29/04* (2006.01)
*A61L 29/08* (2006.01)

(52) U.S. Cl.
CPC ....... *A61L 29/085* (2013.01); *A61M 25/0045* (2013.01); *A61M 2025/0059* (2013.01); *A61M 2210/1078* (2013.01)

(56) References Cited

FOREIGN PATENT DOCUMENTS

| | | |
|---|---|---|
| CN | 205913319 U | 2/2017 |
| CN | 107095638 A | 8/2017 |
| CN | 108095671 A | 6/2018 |
| CN | 207870860 U | 9/2018 |
| CN | 109224248 A | 1/2019 |

B

URETERAL CATHETER STRUCTURE

FIELD OF THE PRESENT DISCLOSURE

The present disclosure relates to the technical field of in vivo catheter structures in medical appliances, and more particularly, to a ureteral catheter structure.

BACKGROUND OF THE PRESENT DISCLOSURE

A ureteroscope is an endoscope for diagnosing and treating diseases in the upper urinary tract by means of special instruments, with only a minimal incision into the human body, which significantly reduces the damage to tissues, and therefore promotes the recovery of the body, shortens the treatment, and improves the curative effect. In this sense, it represents major progress in the endoscope technology, and its clinic application reforms the traditional concept that it is difficult to perform direct observation and examination at ureter, renal pelvis, renal calyces etc., and an invasive surgery is necessary for upper urinary tract diseases. The current ureteroscope in clinic includes two types, namely, rigid ureteroscopes and flexible ureteroscopes. The rigid ureteroscope has the advantages of good directionality, convenience in operation and insertion, but has blind areas in certain visual fields and operations. The flexible ureteroscope can eliminate blind areas in visual fields and operations, but has a soft body, is poor in controllability and difficult to operate, requires a long-term training before practicing with it, and is expensive and easy to damage.

A prior Chinese patent disclosure No. CN1543907A discloses a minimally invasive endoscope for diagnosis and treatment of upper urinary tract diseases, which is a novel ureteroscope composed of a bending body end, a rigid body, and an operation key for controlling bending movement of a rear end of the body on a rear operation handle thereof.

According to the above solution, in the rigid ureteroscope, the rear end of the body can be bent by 0-180 degrees in two opposite directions to conveniently enter the renal calyces. However, in actual production and processing, the hardness of the rigid ureteroscope is uniform as the material of the whole rigid ureteroscope is substantively the same, and when the ureteroscope at the tail end is bent, the ureteroscope at the front end is easily bent or wound, as a result, the detection position of the tail end of the ureteroscope may produce more movement, which affects the use and detection effects.

SUMMARY OF THE PRESENT DISCLOSURE

It is an object of the present disclosure to provide a ureteral catheter structure, advantageous for having a multi-section structure so that a tail end of the ureteral catheter can be independently bent in multiple sections to render a better detection effect.

The above object is achieved by means of the following technical solution, i.e., a ureter catheter structure, including a catheter body, wherein the catheter body includes a stepped braided tube, a bending tube, and a plastic catheter tip which are spliced with each other, a first stainless steel outer tube supports and connects the stepped braided tube and the bending tube at a splice therebetween, and a first PET heat-shrinkable film is coated on the first stainless steel outer tube;

A second stainless steel outer tube supports and connects the bending tube and the plastic catheter tip at a position therebetween, a second PET heat-shrinkable film is covered on the second stainless steel outer tube, a traction wire is provided within the catheter body, one end of the traction wire is fixed on the bending tube, and the other end of the traction wire passes through the stepped braided tube, and a heat-shrinkable sleeve is provided outside the bending tube.

According to the above configuration, the ureteral catheter structure integrates multiple sections and includes the stepped braided tube, the bending tube and the plastic catheter tip; a plurality of splices exist, connection is realized by adopting the first stainless steel outer tube at the splices, and then the first PET heat-shrinkable film and the second PET heat-shrinkable film are wrapped on the first stainless steel outer tube and the second stainless steel outer tube, respectively, to achieve sealing and fixing effects. Specifically, the stepped braided tube is relatively hard, and the bending tube has a good bending capability, so the bending tube is easier to bend than the stepped braided tube, hence the bending tube can be bent independently, the side of bending tube nearer the plastic catheter tip is bent first and is bent to a smaller degree away from the plastic catheter tip. In such a bending process, a good bending gradient is formed in the overall structure. That is, an orientation of the plastic catheter tip can be stably changed along with the action of the traction wire, and the plastic catheter tip is provided with a good detection visual angle.

The present disclosure is further configured such that the bending tube is provided along a length thereof with a plurality of inner fasteners, and the traction wire passes through the plurality of inner fasteners and is fixed in the inner fasteners nearer the plastic catheter tip.

According to the above configuration, the traction wire is relatively fixed by the inner fastener, which limits the swinging of the traction wire, so that the traction wire is more stable in the bending tube and not likely to damage a lead therein, and the traction wire moves stably with the help of the inner fasteners.

The present disclosure is further configured such that the bending tube is provided along the length thereof with a plurality of arc-shaped contraction slots and a mounting recess, the inner fastener is a buckle, limiting wings extend from both sides of the buckle, the mounting recess is used for embedding the buckle, and the limiting wings of the buckle are pressed to fit external to the mounting recess.

According to the above configuration, the arc-shaped contraction slot is used for the bending of the bending tube because it provides sufficient room for the deformation when bending, and the bending tube is thus easier to bent. The inner fastener is actually a buckle in a shape similar to an umbrella, limiting wings extend from both sides of the fastener and are pressed against an outer wall of the bending tube, and then the buckle can be fixed by covering the heat-shrinkable sleeve. The buckle allows the traction wire to pass through and limits a range of swinging for the traction wire. The rigidity of the bending tube is lower than the stepped braided tube, and the bending tube is provided with better flexibility by means of the contraction slot, hence the bending tube is easier to bend.

The present disclosure is further configured such that the contraction slots are uniformly arranged along a peripheral surface of a sidewall of the bending tube, and adjacent contraction slots along the length of the bending tube are staggered.

According to the above configuration, a plurality of contraction slots are arranged in a staggered manner. On one hand, the bending tube can retain better bending performance; on the other hand, the staggering contraction slots provide the bending tube with better structural strength, and the bending tube is subjected to uniform stress at each position.

The present disclosure is further configured such that the contraction slot of the bending tube distal to the plastic catheter tip is of an Ω-shaped configuration.

According to the above configuration, the contraction slot distal to the plastic catheter tip is of an Ω-shaped configuration, as such, a protruding Ω-shaped configuration can abut against the heat-shrinkable sleeve. When the bending tube is bent, the bending tube can have strong elastic restoring force at a portion distal to the plastic catheter tip through elastic contraction of the heat-shrinkable sleeve, and the bending tube at this portion can be quickly restored to a straightened state, which features good operability.

The present disclosure is further configured such that the stepped braided tube is provided with an inner lining tube body for fitting the first stainless steel outer tube.

According to the above configuration, the inner lining tube body cooperates with the first stainless steel outer tube so that the first stainless steel outer tube is facilitated to align, and the first stainless steel outer tube can better cover a splicing gap between the stepped braided tube and the bending tube.

The present disclosure is further configured such that the bending tube is divided into a plurality of bending sections along the length of the bending tube, the inner fastener is an inner convex ring, the bending sections are inwardly stamped to form the inner convex ring through which the traction wire passes, with one end of the traction wire being engaged with the inner convex ring and the other end of the traction wire passing through the stepped braided tube.

According to the above configuration, the bending tube employs a plurality of bending sections. The configuration of bending sections has high winding flexibility and can adapt to the winding of the whole bending tube. Further, the inner convex ring is formed through stamping, hence no additional installation is required, and steps for assembling are simplified.

The present disclosure is further configured such that the bending section is provided with a guide tab, and a guide notch fitting the shape of the guide tab, and the guide tab and the guide notch of adjacent bending sections are matched with each other.

According to the above configuration, the guide tab on the bending section can enable the adjacent bending sections to be more flexible in winding, reducing the relative rotation resistance between the adjacent bending sections. Moreover, the guide tab is matched with the guide notch, so that the adjacent bending sections are not easy to separate, and the stability of the splices among the bending sections is improved.

The present disclosure is further configured such that an embedding groove is formed on an inner side of the stepped braided tube, a stainless steel inner tube is embedded in the embedding groove, the stainless steel inner tube is spliced with an end of the bending section, and the bending section and the stainless steel inner tube are connected by being sleeved in a first stainless steel outer tube; the bending section, the first stainless steel outer tube, and the stepped braided tube are bonded through a PTFE heat-shrinkable tube.

According to the above configuration, the embedding groove can be used for embedding the stainless steel inner tube therein, and the embedded stainless steel inner tube then supports and connects a bending section at the tail end and the stepped braided tube, hence a gap between the stepped braided tube and the bending section is sealed. Besides, the first stainless steel outer tube is sleeved on the bending sections and the stainless steel inner tube, and related parts are bonded through the PTFE heat-shrinkable tube, hence the structural stability and the waterproof performance at the connections are improved.

The present disclosure is further configured such that the first stainless steel outer tube and the first PET heat-shrinkable film, the second stainless steel outer tube and the second PET heat-shrinkable film, the bending tube and the heat-shrinkable sleeve are fixedly connected through UV glue, respectively.

According to the above configuration, several splices are all fixed through the UV glue, the stability of the connection between the first PET heat-shrinkable film and the second PET heat-shrinkable film is improved, and good overall waterproof performance is ensured.

In summary, the present disclosure has the following advantageous effect:

1. The multi-section structure provides a multi-section bending gradient, the bending performance of the bending tube is better, and the bending tube can be bent earlier than the stepped braided tube, hence the bending performance of the front sections is better, and the detection can be conducted more stably;
2. In the multi-section structure, the traction wire are not easy to swing because of the inner fasteners, the sealing performance is improved because of a hierarchical arrangement of the structures, and good waterproof performance is ensured.

LIST OF REFERENCE NUMERALS IN THE DRAWINGS

Figure 1:
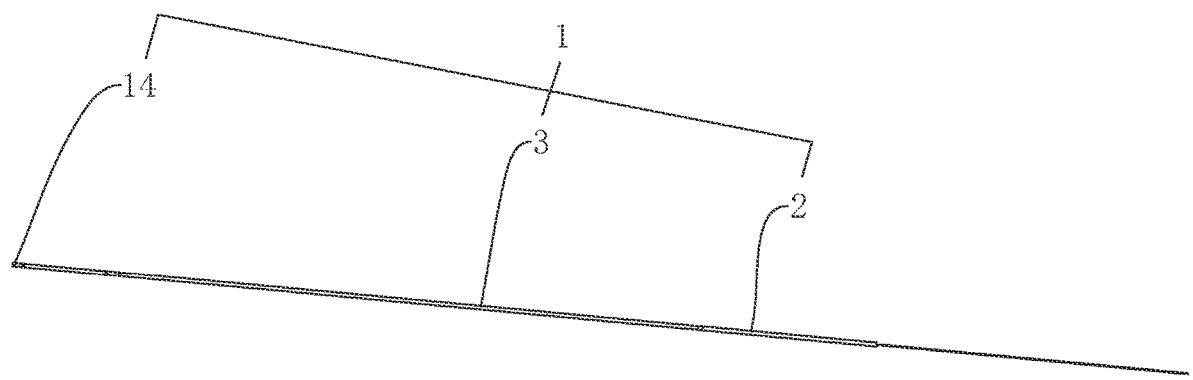
FIG. 1 is a schematic view showing an overall structure of Embodiment 1.

1 catheter body
2 stepped braided tube
21 inner lining tube body
22 embedding groove
3 bending tube
31 contraction slot
32 mounting recess
33 bending section
331 inner convex ring
332 guide tab
333 guide notch
4 first stainless steel outer tube
5 first PET heat-shrinkable film
6 second stainless steel outer tube
7 second PET heat-shrinkable film
8 traction wire
9 heat-shrinkable sleeve 10 buckle
12 stainless steel inner tube
13 PTFE heat-shrinkable tube
14 plastic catheter tip

DESCRIPTION OF THE EMBODIMENTS

The present disclosure will now be described in further detail with reference to the accompanying drawings.

Embodiment 1: referring to FIG. 1, which discloses a ureteral catheter structure including a catheter body 1, wherein the catheter body 1 includes a stepped braided tube 2, a bending tube 3, and a plastic catheter tip 14.

Figure 2:
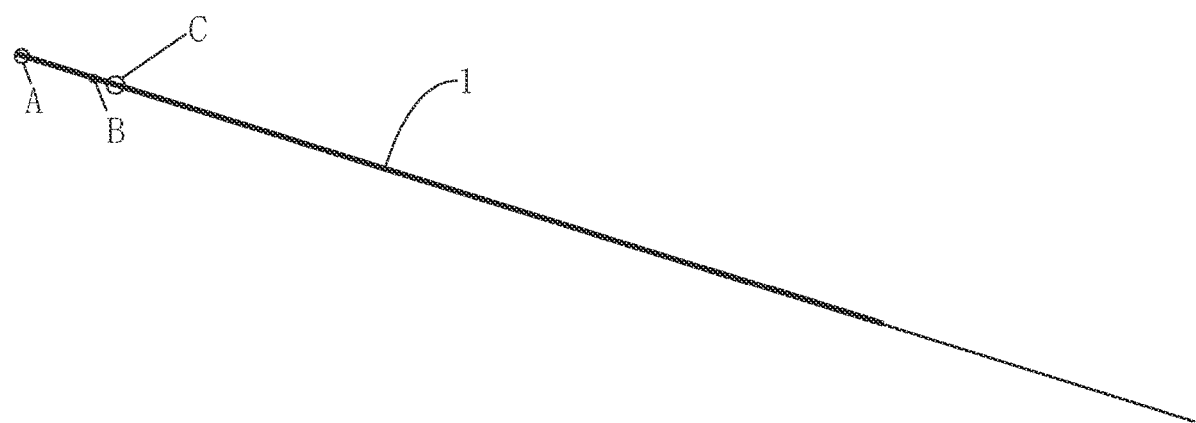
FIG. 2 is a schematic view showing an interior structure of Embodiment 1.
Figure 5:
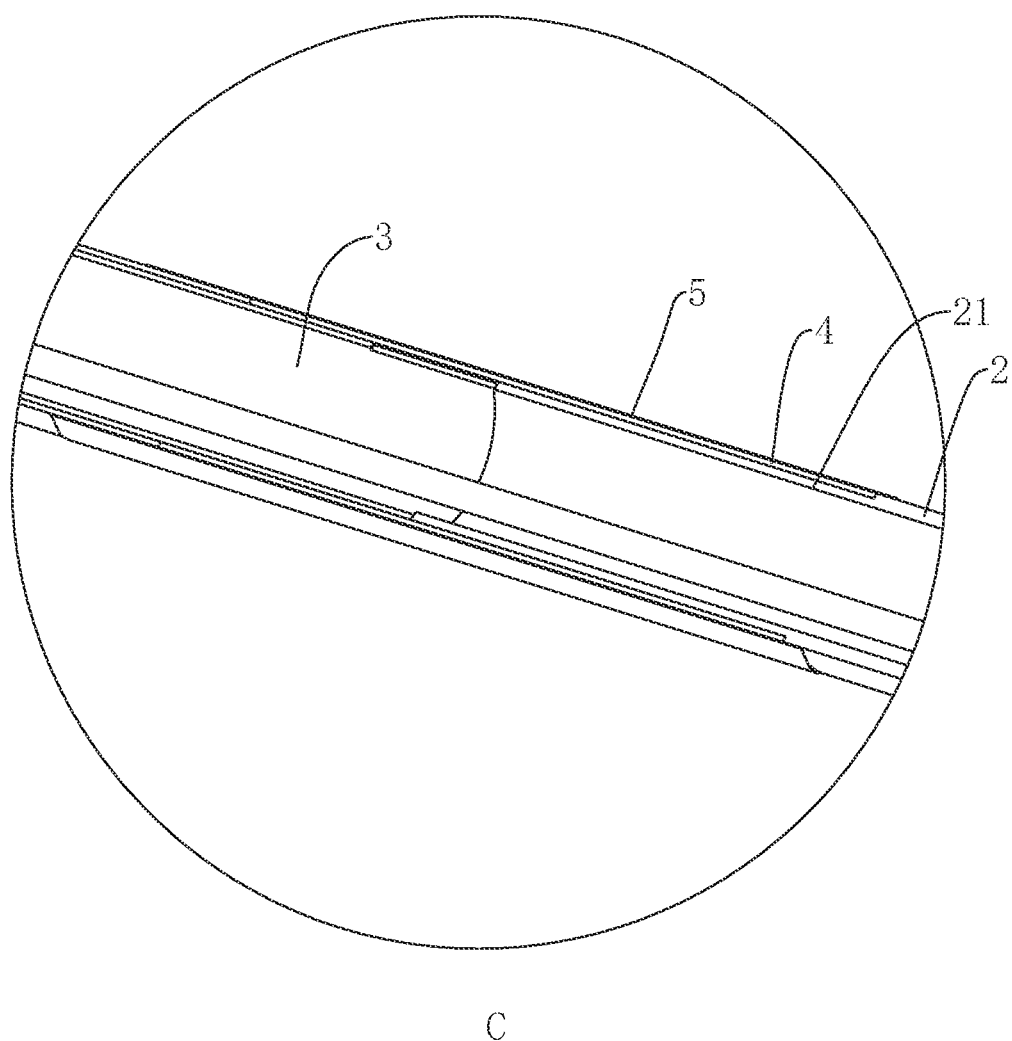
FIG. 5 is an enlarged view at C of FIG. 2.
Figure 6:
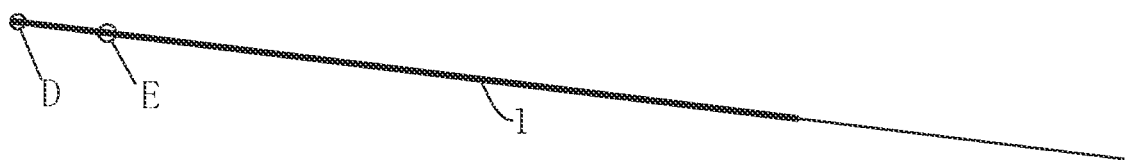
FIG. 6 is a schematic view showing an interior structure of Embodiment 2.

Referring to FIGS. 2 and 5, the stepped braided tube 2 may be made of a nickel-titanium alloy material, the stepped braided tube 2 is spliced with the bending tube 3, a splice between the stepped braided tube 2 and the bending tube 3 is covered by a first stainless steel outer tube 4, the first stainless steel outer tube 4 is covered by a first PET heat-shrinkable film 5 externally, and the first PET heat-shrinkable film 5 can support and connect these components after heat-shrinkable coating.

The stepped braided tube 2 is provided with an inner lining tube body 21 to enable an outer wall of the stepped braided tube 2 to form a stepped shaft shoulder, and the inner lining tube body 21 can be used for the first stainless steel outer tube 4 to slide and fit therein, to improve the connection tightness of the first stainless steel outer tube 4 when abut-joined.

Figure 3:
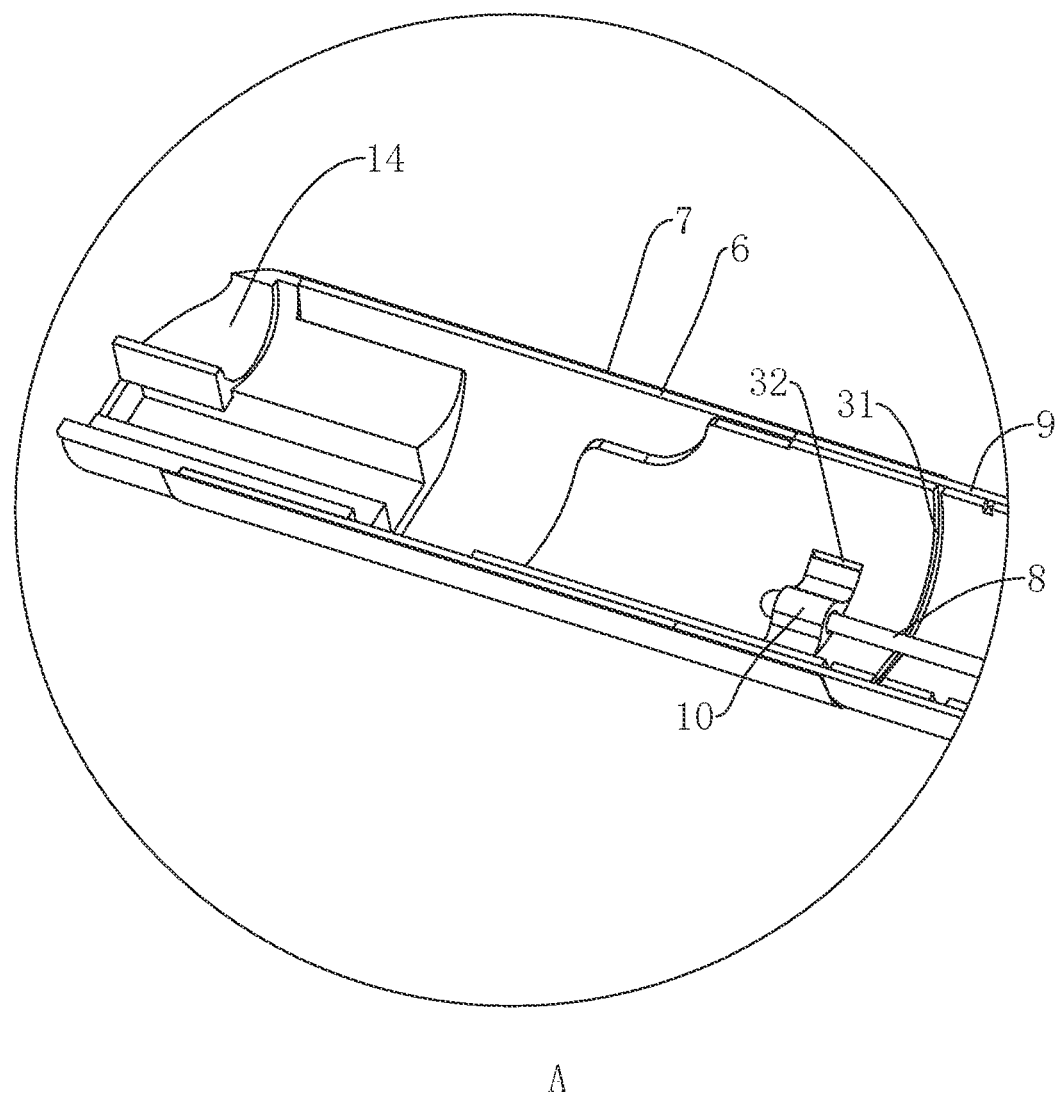
FIG. 3 is an enlarged view at A of FIG. 2.
Figure 4:
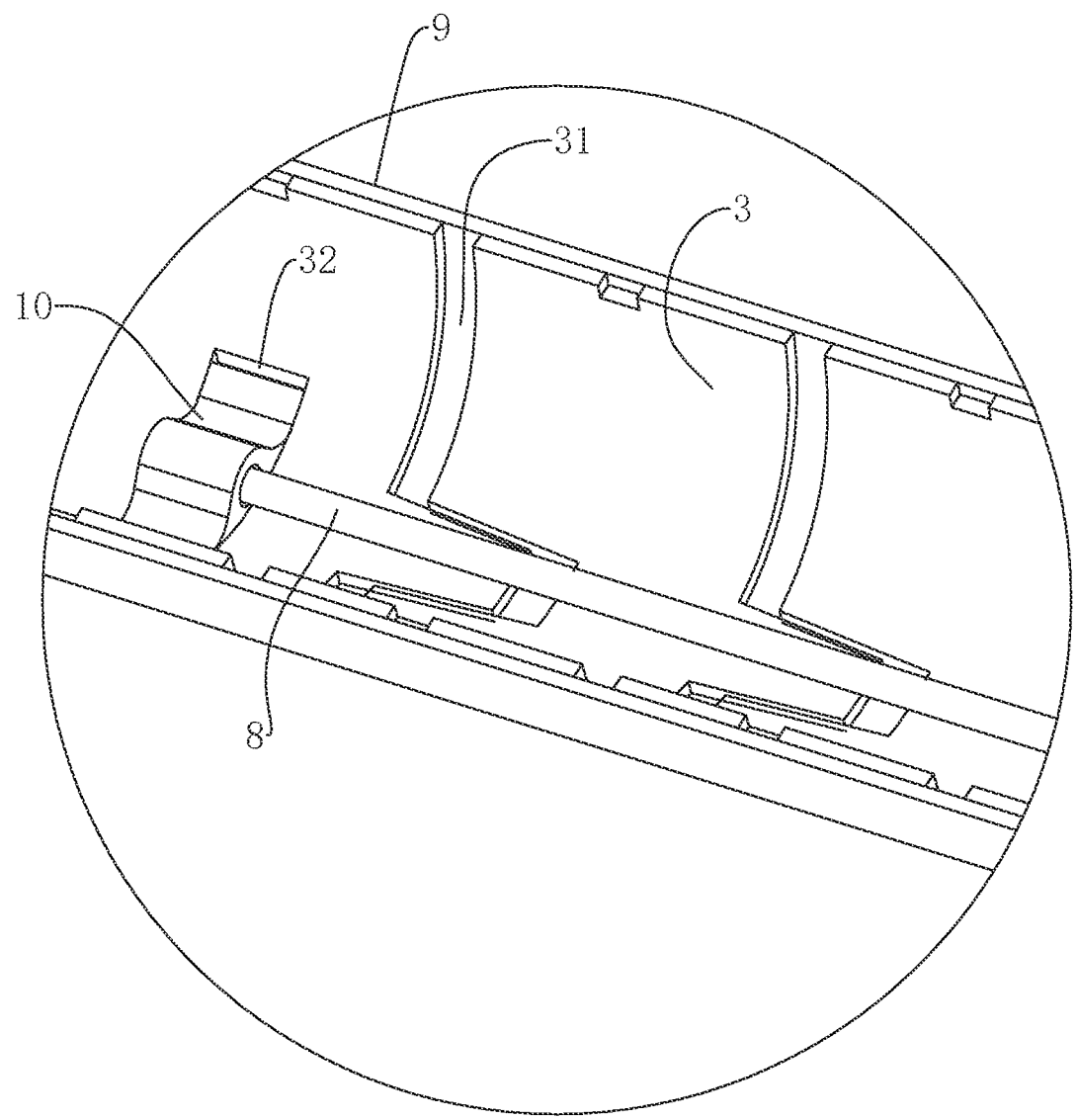
FIG. 4 is an enlarged view at B of FIG. 2.

Referring to FIGS. 3 and 4, the bending tube 3 has a plurality of contraction slots 31 and a mounting recess 32 along a length thereof, and the mounting recess 32 is of an arc-shaped structure. A buckle 10 is embedded in the mounting recess 32, limiting wings (not shown) extend from both sides of the buckle 10. The limiting wings are pressed against an outer wall of the mounting recess 32. An outer wall of the bending tube 3 is wrapped with the heat-shrinkable sleeve 9, and the buckle 10 is pressed tightly through the heat-shrinkable sleeve 9, so the buckle 10 is engaged tightly with the mounting recess 32. The buckle 10 allows the traction wire 8 to pass through. Two traction wires 8 are respectively positioned at opposite positions on an inner wall of the bending tube 3. One end of the traction wire 8 is fixed at a tail end of the bending tube 3 nearer the plastic catheter tip 14, and the other end of the traction wire 8 passes through the stepped braided tube 2. The bending tube 3 is driven to bend by pulling of the two traction wires 8.

Referring to FIGS. 3 and 4, the contraction slots 31 are uniformly arranged along a peripheral surface of a sidewall of the bending tube 3. That is, as shown in FIG. 3, the contraction slots 31 may be provided on upper and lower sidewalls (with corresponding centra angle of smaller than 180 degrees), while the adjacent contraction slots 31 are provided on the left and right sidewalls, staggered with each other. The contraction slot 31 nearer the plastic catheter tip 14 is arc-shaped, while the contraction slot 31 distal to the plastic catheter tip 14 is of an Ω-shaped configuration (FIG. 4). When the bending tube 3 is integrally bent, a protruding Ω-shaped configuration can abut against the heat-shrinkable sleeve 9. By elastic contraction of the heat-shrinkable sleeve 9, the bending tube 3 can have strong elastic restoring force at a portion distal to the plastic catheter tip 14.

Figure 7:
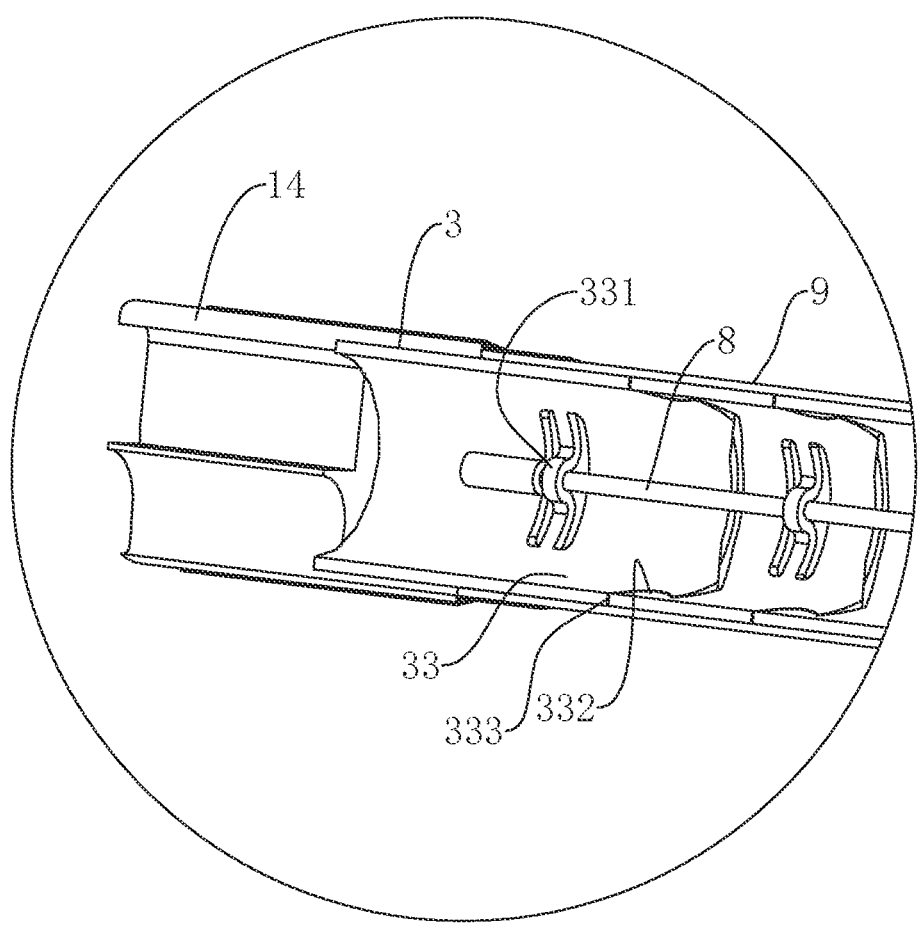
FIG. 7 is an enlarged view at D of FIG. 6.
Figure 8:
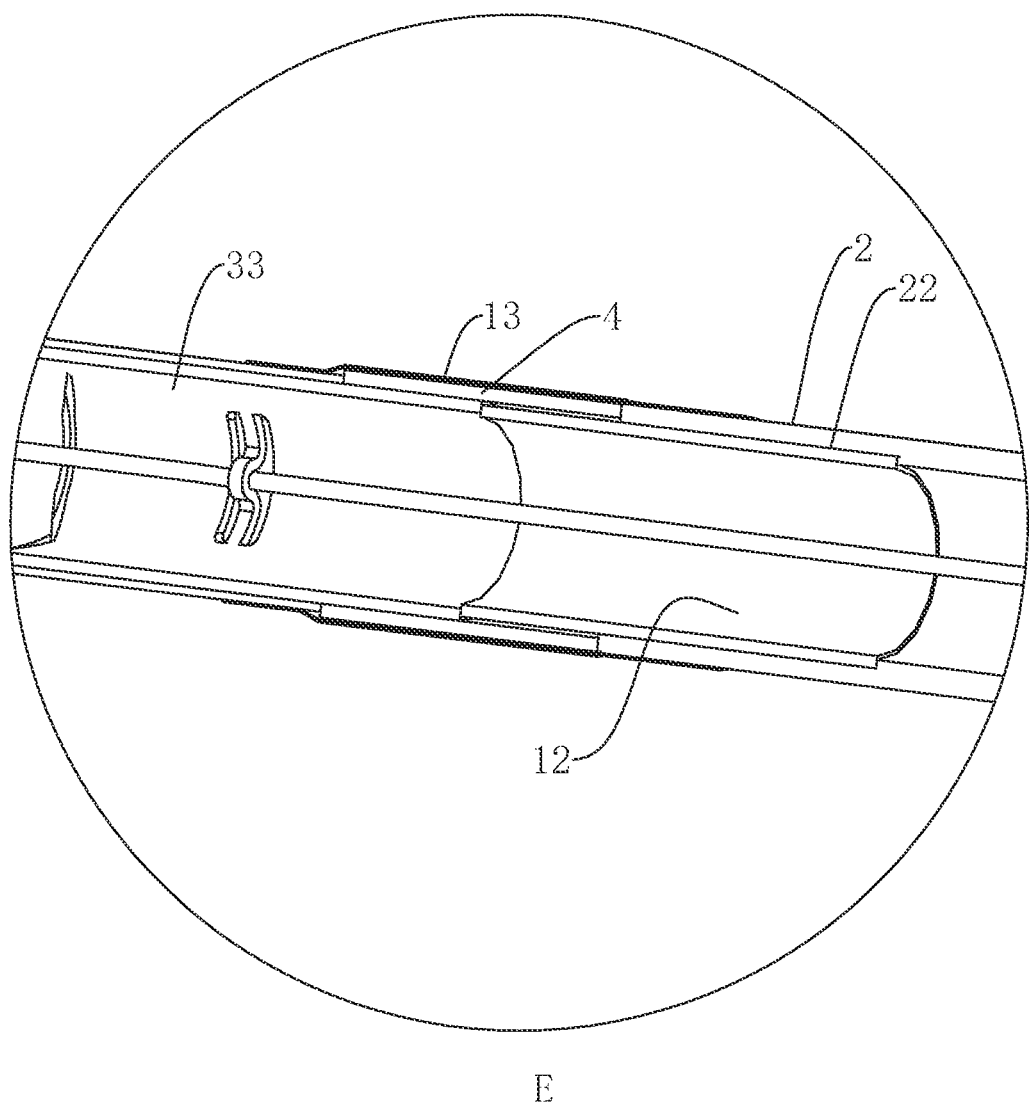
FIG. 8 is an enlarged view at E of FIG. 6.

Embodiment 2: different from Embodiment 1, as shown in FIGS. 7 and 8, the bending tube 3 is divided into a plurality of bending sections 33 along the length thereof, and adjacent bending sections 33 are spliced rather than connected with each other. The bending section 33 is provided with a guide tab 332 and a guide notch 333. The guide tab 332 and the guide notch 333 are matched with each other to limit the relative movement. Moreover, the sliding resistance between the bending sections 33 is small when the bending sections 33 are bent, so the bending sections 33 are facilitated to deform and restore through the heat-shrinkable sleeve 9. The bending section 33 is formed with an inner convex ring 331 through stamping, and the inner convex ring 331 allows the traction wire 8 to pass through and serve as a guide structure to enable the traction wire 8 to pass through the stepped braided tube 2 at the other end.

As shown in FIG. 8, an inner side of the stepped braided tube 2 is provided with an embedding groove 22. A stainless steel inner tube 12 is embedded in the embedding groove 22. The stainless steel inner tube 12 is spliced with one end of the bending section 33. The bending section 33 and the stainless steel inner tube 12 are connected by being sleeved in a first stainless steel outer tube 4. The bending section 33 and the stainless steel inner tube 12 are bonded through a PTFE heat-shrinkable tube 13 after be spliced, and then are fixed to form a multilayer sealed structure.

To improve the bonding firmness and waterproof performance at each splice position, the first stainless steel outer tube 4 and the first PET heat-shrinkable film 5, the second stainless steel outer tube 6 and the second PET heat-shrinkable film 7, and the bending tube 3 and the heat-shrinkable sleeve 9 are fixedly connected through UV glue, respectively.

Figure 9:
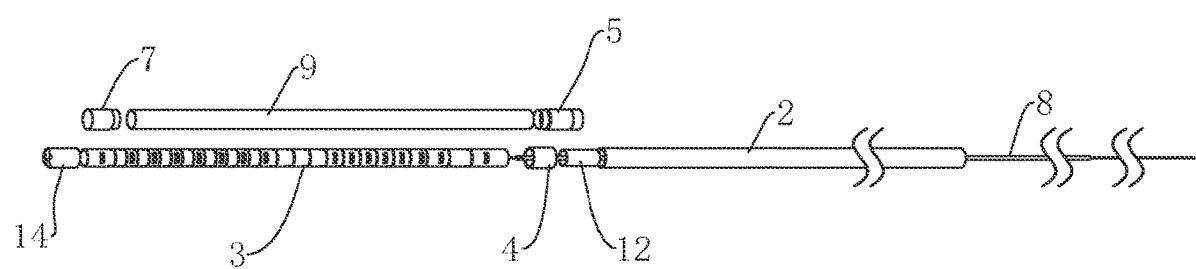
FIG. 9 is an exploded view of Embodiment 2.
Figure 10:
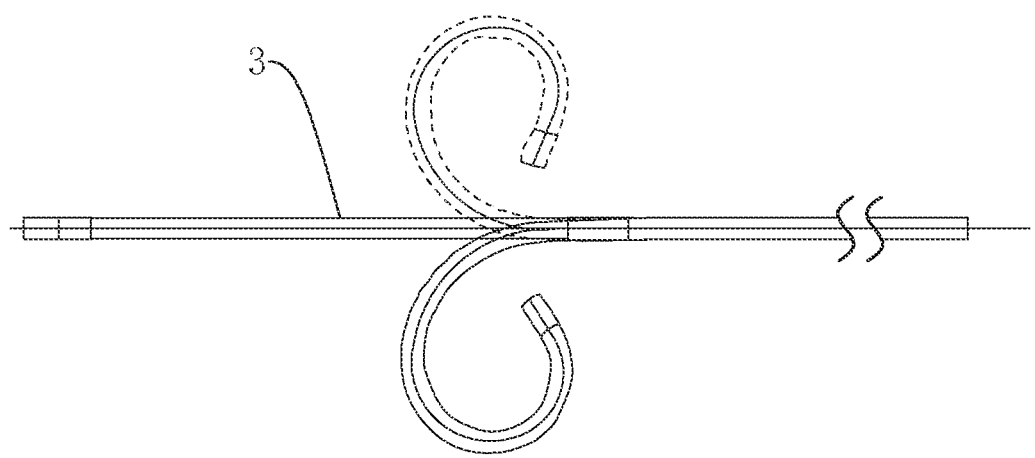
FIG. 10 is a view showing a bent state of Embodiment 2.

FIG. 9 is an exploded view of Embodiment 2, and FIG. 10 is a view of a simulation of a bent state of Embodiment 2, where two extreme cases of a bending angle of the bending tube 3 are shown.

The embodiments of the detailed description of the present invention are all preferred embodiments and are not intended to limit the scope thereof. All equivalent changes that come within the scope of structures, shapes and principles of the present disclosure are to be embraced within the scope thereof.

What is claimed is:

1. A ureteral catheter structure, comprising a catheter body (1), wherein the catheter body (1) comprises a stepped braided tube (2), a bending tube (3), and a plastic catheter tip (14) which are spliced with each other; a first stainless steel outer tube (4) supports and connects the stepped braided tube (2) and the bending tube (3) at a splice therebetween, and a first PET heat-shrinkable film (5) is coated on the first stainless steel outer tube (4);

a second stainless steel outer tube (6) supports and connects the bending tube (3) and the plastic catheter tip (14) at a position therebetween, a second PET heat-shrinkable film (7) is coated on the second stainless steel outer tube (6), a traction wire (8) is provided within the catheter body (1), an end of the traction wire (8) being fixed on the bending tube (3), while the other end passing through the stepped braided tube (2); a heat-shrinkable sleeve (9) is provided outside the bending tube (3).

2. The ureteral catheter structure according to claim 1, wherein the bending tube (3) is provided along a length thereof with a plurality of inner fasteners, through which the traction wire (8) passes and is fixed in the inner fasteners nearer the plastic catheter tip (14).

3. The ureteral catheter structure according to claim 2, wherein the bending tube (3) is provided along the length thereof with a plurality of arc-shaped contraction slots (31) and a mounting recess (32), the inner fastener is a buckle (10), limiting wings extend from both sides of the buckle (10), the mounting recess (32) allows the buckle (10) to be embedded therein, and the limiting wings of the buckle (10) are pressed to fit external to the mounting recess (32).

4. The ureteral catheter structure according to claim 2, wherein the contraction slots (31) are uniformly arranged along a peripheral surface of a sidewall of the bending tube (3), and adjacent contraction slots (31) are staggered along the length of the bending tube (3).

5. The ureteral catheter structure according to claim 3, wherein the contraction slot (31) of the bending tube (3) distal to the plastic catheter tip (14) is of an Q-shaped configuration.

6. The ureteral catheter structure according to claim 2, wherein the stepped braided tube (2) is provided with an inner lining tube body (21) for fitting the first stainless steel outer tube (4).

7. The ureteral catheter structure according to claim 2, wherein the bending tube (3) is divided along the length thereof into a plurality of bending sections (33), the inner fastener is an inner convex ring (331), the bending section (33) is inwardly stamped to form the inner convex ring (331) through which the traction wire (8) passes, with one end of the traction wire (8) being engaged with the inner convex ring (331) and the other end passing through the stepped braided tube (2).

8. The ureteral catheter structure according to claim 7, wherein the bending section (33) is provided with a guide tab (332) and a guide notch (333) adapted to a shape of the guide tab (332), and the guide tab (332) and the guide notch (333) of adjacent bending sections (33) are matched with each other.

9. The ureteral catheter structure according to claim 8, wherein an embedding groove (22) is formed on an inner side of the stepped braided tube (2), a stainless steel inner tube (12) is embedded in the embedding groove (22), the stainless steel inner tube (12) is spliced with an end of the bending section (33), and the bending section (33) and the stainless steel inner tube (12) are connected by being sleeved in a first stainless steel outer tube (4); the bending section (33), the first stainless steel outer tube (4), and the stepped braided tube (2) are bonded through a PTFE heat-shrinkable tube (13).

10. The ureteral catheter structure according to claim 1, wherein the first stainless steel outer tube (4) and the first PET heat-shrinkable film (5), the second stainless steel outer tube (6) and the second PET heat-shrinkable film (7), the bending tube (3) and the heat-shrinkable sleeve (9) are fixedly connected through UV glue, respectively.

\* \* \* \* \*